(12) United States Patent
Burkholz (10) Patent No.: US 11,911,570 B2
(45) Date of Patent: *Feb. 27, 2024

(54) CATHETER SECUREMENT DEVICE WITH WINDOW

(71) Applicant: Becton, Dickinson and Company, Franklin Lakes, NJ (US)

(72) Inventor: Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 416 days.

This patent is subject to a terminal disclaimer.

(21) Appl. No.: 17/217,838

(22) Filed: Mar. 30, 2021

(65) Prior Publication Data

US 2021/0213240 A1 Jul. 15, 2021

Related U.S. Application Data

(63) Continuation of application No. 15/481,739, filed on Apr. 7, 2017, now Pat. No. 10,987,486.

(51) Int. Cl.
*A61M 25/00* (2006.01)
*A61M 25/02* (2006.01)

(52) U.S. Cl.
CPC ............ *A61M 25/00* (2013.01); *A61M 25/02* (2013.01); *A61M 2025/0246* (2013.01); *A61M 2025/0253* (2013.01); *A61M 2025/0266* (2013.01); *A61M 2025/0273* (2013.01)

(58) Field of Classification Search
CPC .. A61M 2025/0246; A61M 2025/0253; A61M 2025/0266; A61M 2025/0273; A61M 25/00; A61M 25/02
See application file for complete search history.

(56) References Cited

U.S. PATENT DOCUMENTS

| | | |
|---|---|---|
| 4,059,105 A | 11/1977 | Cutruzzula |
| 4,324,237 A | 4/1982 | Buttaravoli |
| 4,584,192 A | 4/1986 | Dell et al. |

(Continued)

FOREIGN PATENT DOCUMENTS

| | | |
|---|---|---|
| CN | 104114135 | 10/2014 |
| FR | 3018453 | 9/2015 |

(Continued)

OTHER PUBLICATIONS

ChloraPrep, Enturia, Retrieved from the internet URL: http://www.enturia.com/products/chloraPrep/chloraPrep-product.html, on Oct. 31, 2008, p. 1-3.

(Continued)

*Primary Examiner* — Brandy S Lee
(74) *Attorney, Agent, or Firm* — Kirton McConkie; Whitney Blair; Kevin Stinger (57) ABSTRACT

An anchor system for securing a catheter to a patient may include an anchor pad, which may include a lower surface, an upper surface, and a window extending through the anchor pad. The lower surface may include an adhesive layer to adhere the anchor pad to skin of the patient. The upper surface may include a catheter securement mechanism. The window may provide access to the skin of the patient for application of a topical skin adhesive at a catheter insertion site disposed within the window.

4 Claims, 9 Drawing Sheets

(56) References Cited

U.S. PATENT DOCUMENTS

| | | |
|---|---|---|
| 4,669,458 A | 6/1987 | Abraham et al. |
| 4,716,032 A | 12/1987 | Westfall et al. |
| 4,915,934 A | 4/1990 | Tomlinson |
| 4,925,668 A | 5/1990 | Khan et al. |
| 5,023,082 A | 6/1991 | Friedman et al. |
| 5,512,199 A | 4/1996 | Khan et al. |
| 5,547,662 A | 8/1996 | Khan et al. |
| 5,616,338 A | 4/1997 | Fox, Jr. et al. |
| 5,637,098 A | 6/1997 | Bierman |
| 5,685,859 A | 11/1997 | Kornerup |
| 5,861,440 A | 1/1999 | Gohla et al. |
| 6,051,609 A | 4/2000 | Yu et al. |
| 6,337,357 B1 | 1/2002 | Fukunishi et al. |
| 6,413,539 B1 | 7/2002 | Shalaby |
| 6,488,942 B1 | 12/2002 | Ingemann |
| 6,846,846 B2 | 1/2005 | Modak et al. |
| 6,861,060 B1 | 3/2005 | Luriya et al. |
| 7,198,800 B1 | 4/2007 | Ko |
| 7,268,165 B2 | 9/2007 | Greten et al. |
| 7,651,479 B2 | 1/2010 | Bierman |
| 7,699,810 B2 | 4/2010 | Rosenberg |
| 7,704,935 B1 | 4/2010 | Davis et al. |
| 8,679,066 B2 | 3/2014 | Aviles |
| 9,566,417 B1 | 2/2017 | Propp |
| 10,987,486 B2 * | 4/2021 | Burkholz ............ A61M 25/02 |
| 2001/0016589 A1 | 8/2001 | Modak et al. |
| 2002/0144705 A1 | 10/2002 | Brattesani et al. |
| 2003/0072781 A1 | 4/2003 | Pelerin |
| 2003/0162839 A1 | 8/2003 | Symington et al. |
| 2004/0039349 A1 | 2/2004 | Modak et al. |
| 2004/0112510 A1 * | 6/2004 | Rosenberg ............ A61M 25/02 |
| | | 604/528 |
| 2006/0095008 A1 | 5/2006 | Lampropoulos et al. |
| 2006/0165751 A1 | 7/2006 | Chudzik et al. |
| 2006/0239954 A1 | 10/2006 | Sancho |
| 2008/0075761 A1 | 3/2008 | Modak et al. |
| 2008/0182921 A1 | 7/2008 | Suh et al. |
| 2009/0143740 A1 | 6/2009 | Bierman et al. |
| 2011/0021998 A1 * | 1/2011 | Dikeman ............ A61M 25/02 |
| | | 604/180 |
| 2011/0060295 A1 | 3/2011 | Hen et al. |
| 2013/0150796 A1 | 6/2013 | Souza et al. |
| 2014/0257242 A1 | 9/2014 | Sung et al. |
| 2015/0032057 A1 | 1/2015 | Ashfaque |
| 2015/0224285 A1 | 8/2015 | Howell et al. |
| 2016/0193452 A1 | 7/2016 | Hanson et al. |
| 2018/0161543 A1 | 6/2018 | Burkholz |
| 2018/0289922 A1 | 10/2018 | Burkholz |

FOREIGN PATENT DOCUMENTS

| | | |
|---|---|---|
| JP | H01-500326 | 2/1989 |
| JP | 2008-518664 | 6/2008 |
| JP | 2015505692 | 2/2015 |
| JP | 2015-529115 | 10/2015 |
| JP | 2017-507726 | 3/2017 |
| WO | 02/058774 | 8/2002 |
| WO | 2006/070802 | 7/2006 |
| WO | 2015/035238 | 3/2015 |
| WO | 2018/111443 A1 | 6/2018 |
| WO | 2018186979 W | 10/2018 |

OTHER PUBLICATIONS

Preoperative Skin Preparation and Peri operative Oral Care for the Short-Term Ventilated Patient, Sage Products, Inc., Retrieved from the internet URL: http://www.sageproducts.com/products/ssi-vap-prevention.cfm, on Oct. 31, 2008, p. 1.

Address Multi-Drug Resistant Organisms on the Skin with Early Preop Prep, Sage Products, Inc., Retrieved from the Internet URL: http://www.sageproducts.com/products/ssi-prevention.cfm, on Oct. 31, 2008, p. 1.

Preoperative Skin Preparation for the Surgical Patient, Sage Products, Inc., Retrieved from the internet URL: http://www.sageproducts.com/products/skin-prep.cfm, on Oct. 31, 2008, p. 1.

Clinell Alcoholic 2% Chlorhexidine, Gama Healthcare, Retrieved from the internet URL: http://www.gamahealthcare.com/clinellaca2c.html, on Nov. 7, 2008, p. 1-3.

\* cited by examiner

CATHETER SECUREMENT DEVICE WITH WINDOW

RELATED APPLICATIONS

This application is a continuation of U.S. patent application Ser. No. 15/481,739, filed Apr. 7, 2017, and entitled CATHETER SECUREMENT DEVICE WITH WINDOW, which is hereby incorporated by reference in its entirety.

BACKGROUND

A clinician may insert a vascular access device into a blood vessel of a patient to infuse fluid and/or draw blood. The vascular access device may first penetrate skin of the patient at an insertion site, and when the vascular access device is properly placed within the blood vessel, the clinician may apply a skin adhesive at the insertion site to secure the vascular access device. In order to apply the skin adhesive at the insertion site, the clinician may hold the inserted catheter in one hand and use another hand to open an adhesive container and apply the skin adhesive. After applying the skin adhesive to the insertion site, the clinician may hold the vascular access device while the skin adhesive dries. Securing the vascular access device via the skin adhesive may thus be a difficult and messy process that may result in dislodgement of the vascular access device, ineffective application of the skin adhesive through application of too much or too little of the skin adhesive, or adhering of the skin adhesive to a hand or glove of the clinician. Accordingly, there is a need in the art for devices, systems, and methods that provide securement of the vascular access device in a controlled, safe manner.

BRIEF SUMMARY

The present disclosure relates generally to devices, systems, and associated methods to secure and stabilize a vascular access device inserted into a blood vessel of a patient. In some embodiments, an anchor system to secure the vascular access device to the patient may include an anchor pad, which may include a lower surface, an upper surface, and a window extending through the anchor pad. In some embodiments, the lower surface may include an adhesive layer to adhere the anchor pad to skin of the patient. In some embodiments, the window may provide access to the skin of the patient for application of a topical skin adhesive at an insertion site of the vascular access device, the insertion site being disposed within the window.

In some embodiments, the skin adhesive may be disposed within the window to secure the vascular access device in place at the insertion site. In some embodiments, the window may enclose the insertion site, which may facilitate controlled and contained application of the skin adhesive at the insertion site. In further detail, the skin adhesive may contact the skin of the patient within the window, but may be prevented or discouraged from contacting skin of the patient outside of the window, reducing a likelihood of a messy application of the skin adhesive. In some embodiments, the skin adhesive may provide localized stabilization of the vascular access device at the insertion site and/or may provide a seal around the vascular access device at the insertion site, which may prevent infection. The skin adhesive may also increase an indwell time for the vascular access device.

In some embodiments, a securement mechanism may be disposed on the upper surface of the anchor pad and may secure the vascular access device to the anchor pad. In some embodiments, the securement mechanism may include an adhesive well. In some embodiments, the securement mechanism may include a retainer capable of receiving a portion of the vascular access device. In some embodiments, the retainer may be coupled to the upper surface.

In some embodiments, the anchor pad may include a release liner that may cover the adhesive layer and may be removed prior to adhering the anchor pad to the skin of the patient. In some embodiments, the anchor pad may include a slot that may extend from the window to an exterior of the anchor pad. The slot may allow the vascular access device to be inserted into the patient prior to positioning and securing the anchor pad to the skin of the patient.

In some embodiments, a method of securing the vascular access device may include providing the anchor pad and/or the securement mechanism. In some embodiments, the method may include inserting the vascular access device into the patient at the insertion site. In some embodiments, the method may include adhering the anchor pad to the skin of the patient via the adhesive layer. In some embodiments, the method may include securing a portion of the vascular access device within the securement mechanism. In some embodiments, the method may include applying the skin adhesive at the insertion site and/or proximate the insertion site within the window after the vascular access device is inserted at the insertion site and after the anchor pad is adhered to the skin of the patient.

In some embodiments in which the anchor pad includes the slot, adhering the anchor pad to the skin of the patient via the adhesive layer may include placing the window around a vascular access device via the slot, the vascular access device having been previously inserted at the insertion site. In some embodiments, adhering the anchor pad to the skin of the patient via the adhesive layer may include removing the release liner covering the adhesive layer.

BRIEF DESCRIPTION OF THE SEVERAL VIEWS OF THE FIGURES

In order that the manner in which the above-recited and other features and advantages of the invention will be readily understood, a more particular description of the devices, systems, and associated methods to secure and stabilize a vascular access device briefly described above will be rendered by reference to specific embodiments thereof, which are illustrated in FIGS. 1-4. Understanding that these Figures depict only typical embodiments and are not, therefore, to be considered to be limiting of its scope, the invention will be described and explained with additional specificity and detail through the use of the accompanying Figures in which.

DETAILED DESCRIPTION

The presently preferred embodiments of the described invention will be best understood by reference to the Figures, wherein like parts are designated by like numerals throughout. It will be readily understood that the components of the present invention, as generally described and illustrated in the Figures in the present disclosure, could be arranged and designed in a wide variety of different configurations. Thus, the following more detailed description of the embodiments, represented in FIGS. 1 through 4, is not intended to limit the scope of the invention, as claimed, but is merely representative of some embodiments of the invention.

Figure 1A:
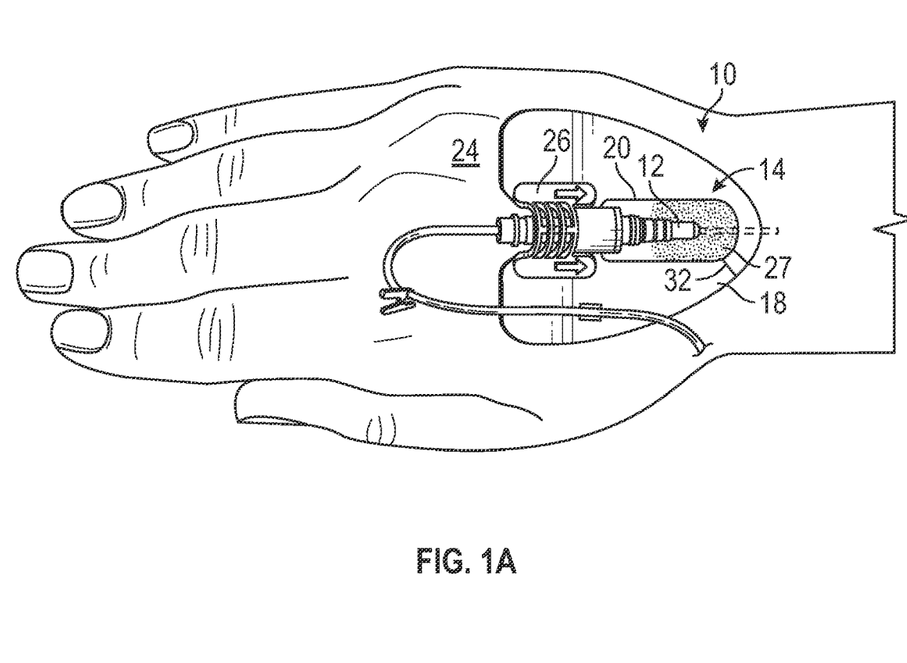
FIG. 1A is a top view of an example anchor system, illustrating an example catheter coupled to the anchor system, according to some embodiments.
Figure 1B:
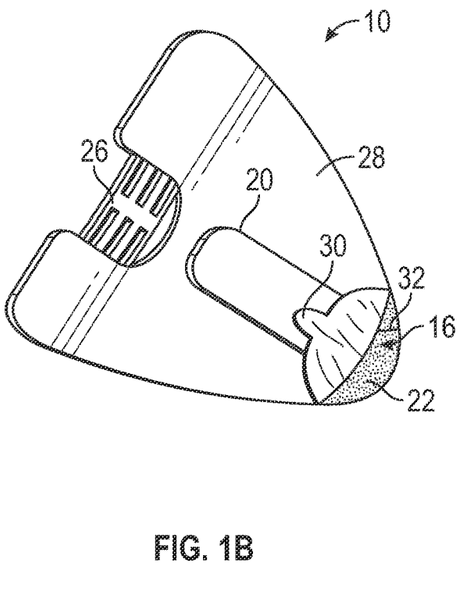
FIG. 1B is a lower perspective view of the anchor system of FIG. 1A, according to some embodiments.

Referring to FIGS. 1A-1B, an example anchor system 10 for securing a catheter 12 to a patient is illustrated. It is understood, however, that the anchor system 10 may be utilized in connection with other vascular access devices, including, but not limited to, fluid supply and drainage lines, feeding tubes, chest tubes, scopes, connectors, adaptors, electrical wires and cables, and the like, any of which may be secured to the patient by the anchor system 10.

In some embodiments, the anchor system 10 may include an anchor pad 14, which may include various shapes and sizes. In some embodiments, the anchor pad 14 may include a lower surface 16, an upper surface 18, and a window 20 extending through the anchor pad 14. In some embodiments, the lower surface 16 may include an adhesive layer 22 to adhere the anchor pad 14 to skin 24 of the patient.

In some embodiments, the upper surface 18 may include a catheter securement mechanism, such as, for example, a retainer or another suitable mechanism. In some embodiments, the retainer 26 may be coupled to the upper surface 18 and may be capable of receiving a portion of the catheter 12. In some embodiments, the window 20 may provide access to the skin 24 of the patient for application of a topical skin adhesive 27 at an insertion site of the catheter 12, the insertion site being disposed within the window 20. In some embodiments, a catheter tubing of the catheter 12 may extend beneath the anchor pad 14, as illustrated in FIGS. 1A, for example, into a blood vessel of the patient. In some embodiments, the retainer 26 may include a clip, clasp, clamp, snap, button, strap, Velcro® or any other suitable mechanism for securing the portion of the catheter 12 to the anchor pad 14. In some embodiments, the retainer 26 may allow selective coupling of the portion of the catheter 12 to the anchor pad 14.

In some embodiments, the skin adhesive 27 may be disposed within the window 20 to secure the catheter 12 in place at the insertion site. In some embodiments, the window 20 may enclose the insertion site, which may facilitate controlled and contained application of the skin adhesive 27 at the insertion site. In further detail, the skin adhesive 27 may contact the skin 24 of the patient within the window 20 and/or a portion of the anchor pad 14 proximate the window 20, but may be prevented or discouraged from contacting skin 24 of the patient outside of the window 20, reducing a likelihood of a messy application of the skin adhesive 27. In some embodiments, the skin adhesive 27 may provide localized stabilization of the catheter 12 at the insertion site and/or may provide a seal around the catheter 12 at the insertion site, which may prevent infection. The skin adhesive 27 may also increase an indwell time for the catheter 12.

In some embodiments, the catheter 12 may be inserted into the patient prior to application of the skin adhesive 27 to the insertion site. Given the difficultly and usability challenges of holding the catheter 12 in position while applying the skin adhesive 27 to the insertion site, it may be advantageous to provide a means of securement of the catheter 12, such as the anchor pad 14 and the catheter securement mechanism, prior to application of the skin adhesive 27. Thus, in some embodiments, insertion of the catheter 12 and placement of the anchor pad 14 on the skin of the patient may occur prior to application of the skin adhesive 27. The anchor pad 14 and the catheter securement mechanism may facilitate greater control and accuracy in placement of the skin adhesive 27 at the insertion site, reduce an amount of skin adhesive 27 required, reduce a likelihood of a messy application of the skin adhesive 27, and reduce a risk of the catheter 12 becoming dislodged due to unintentional movement during application of the skin adhesive 27. Further, the anchor pad 14 and the catheter securement mechanism may eliminate a need for the clinician to hold the catheter 12 while the skin adhesive 27 dries, which may reduce a likelihood of the skin adhesive 27 bonding to a hand or glove of the clinician.

In some embodiments, an outer edge of the window 20 may be spaced apart from an outer edge of the anchor pad 14. In further detail, in some embodiments, the window 20 may be inset from the outer edge of the anchor pad 14. In some embodiments, the securement mechanism may be aligned with the window 20 such that the catheter 12 may extend outwardly from the securement mechanism to the window 20. In some embodiments, the catheter 12 may extend through a middle portion of the window 20.

In some embodiments, the skin adhesive 27 may include cyanoacrylate or another suitable glue or bonding material. In some embodiments, cyanoacrylate may include liquid monomers and may polymerize on contact with the skin, creating a flexible and/or semi-rigid layer. In these and other embodiments, liquid cyanoacrylate may be applied at the insertion site within the window 20 and may cure to a solid form within a period of seconds.

In some embodiments, the adhesive layer 22 may include any type or form of adhesive that is suitable for use with the methods and embodiments discussed in the present disclosure. In some embodiments, the adhesive layer 22 may be a spray-on adhesive, adhesive film, or any other type of adhesive application. In some embodiments the adhesive layer 22 may be formed of or include a polymer-based pressure sensitive adhesive. For example, when a polymer-based pressure sensitive adhesive is used in the adhesive layer 22, a bond may formed between the adhesive layer 22 and the skin 24 of the patient by applying light pressure between anchor pad 14 and the skin 24. In some embodiments, the adhesive layer 22 may include a slight liquid carrier that facilitates bonding with the skin 24. In some embodiments, the adhesive layer 22 may include a single-use glue, such that the adhesive layer 22 loses its adhesive properties once removed from the skin 24. In some embodiments, the adhesive layer 22 may include an antimicrobial agent to aid in maintaining sterility of the insertion site. In some embodiments, the adhesive layer 22 may include a multiple-use glue, which may allow the anchor pad 14 to be applied repeatedly.

In some embodiments, the window 20 may provide access to skin 24 of the patient for application of the skin adhesive 27 and/or a cleaning or disinfection agent at the insertion site of the catheter 12. In some embodiments, the cleaning agent may be disposed within the window 20 and may contact the skin 24 of the patient within the window 20. In some embodiments, the skin adhesive 27 and/or the cleaning agent may be prevented or discouraged from contacting the skin 24 of the patient outside of the window 20 and/or beyond an outer edge of the anchor pad 14. In some embodiments, the skin adhesive 27 and/or the cleaning agent may be wicked or pulled into the anchor pad 14 from the window 20 but may not contact the skin 24 beyond the outer edge of the anchor pad 14.

In some embodiments, a material of the anchor pad 14 may absorb a portion of the skin adhesive 27 and/or the cleaning agent and prevent spreading of the skin adhesive 27 and/or cleaning agent beyond the outer edge of the anchor pad 14. In some embodiments, the skin adhesive 27 and/or the cleaning agent may be contained within the window 20. In some embodiments, the anchor pad 14 may include any suitable medical grade material. In some embodiments, in addition to the adhesive layer 22, the anchor pad 14 may include a cloth layer and/or a foam layer. In some embodiments, the cloth layer may include the upper surface 18. In some embodiments, the foam layer may include the upper surface 18. In some embodiments, the cloth layer may be non-woven or woven. In some embodiments, the anchor pad 14 may include one or more antimicrobial agents, which may be applied in a film or otherwise.

In some embodiments, the retainer 26 may be coupled to the upper surface 18 through any number of means, such as, for example, mounting, attaching, etc. In some embodiments, the retainer 26 may be coupled to the upper surface 18 by means of cyanoacrylate or another bonding material. The retainer 26 may increase a force necessary to dislodge the catheter 12 at the insertion site. In some embodiments, the retainer 26 may include any mechanism configured to engage and secure the catheter 12 within the retainer 26. In some embodiments, the retainer 26 may prevent movement of the catheter 12 in a distal and/or proximal direction. For example, the retainer 26 may have at least one abutment. In some embodiments, the retainer 26 may include a channel shaped to receive a catheter hub or another portion of the catheter 12. In some embodiments, the retainer 26 may be similar to or include any suitable retainer of a StatLock® external stabilization device (Bard Medical) or another external stabilization device.

In some embodiments, the retainer 26 may be constructed as a single piece or from multiple different pieces. For example, the entire retainer 26 may be formed by injection molding or components of the retainer 26 may be formed separately and thereafter joined together. In some embodiments, the retainer 26 or portions thereof may be rigid or flexible. The retainer 26 may be constructed of one or more materials, which may include, for example, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics, or another suitable material.

In some embodiments, the anchor pad 14 may include a slit or slot 32 that may extend from the window 20 to an exterior of the anchor pad 14. In some embodiments, the slot 32 may allow the catheter 12 to be inserted into the patient prior to positioning and securing the anchor pad 14 to the skin 24 of the patient. In some embodiments, the anchor system 10 may be placed over the catheter 12, which may be secured to the retainer 26 via a snap mechanism or similar mechanism. In these embodiments, the catheter 12 may be inserted at the insertion site prior to positioning and securing the anchor pad 14 to the patient without presence of the slot 32.

Referring now to FIG. 1B, in some embodiments, the anchor pad 14 may include a release liner 28 that may cover the adhesive layer 22 and may be removed prior to adhering the anchor pad 14 to the skin 24 of the patient. In some embodiments, the release liner 28 may include any material or combination of materials that permit temporary bonding between the release liner 28 and the adhesive layer 22. In some embodiments, the release liner 28 may be divided into multiple pieces to ease attachment of the anchor pad 14 to the skin 24 of the patient. In some embodiments, the release liner 28 may include an aperture corresponding to the window 20, as illustrated in FIG. 1B, or the release liner 28 may cover the window 20. In some embodiments, the release liner 28 may include paper, plastic, or another suitable material. In some embodiments, the release liner 28 may include one or more antimicrobial agents.

In some embodiments, the release liner 28 may include one or more pull-tabs 30 to facilitate removal of the release liner 28 from the adhesive layer 22. In some embodiments, the release liner may be removed by pulling or peeling the release liner 28 in a distal direction, in a proximal direction, or toward one or more sides of the anchor pad 14. In some embodiments, the pull-tabs 30 may be designed in a variety of configurations and need not be disposed along a centerline of the anchor pad 14.

Figure 1C:
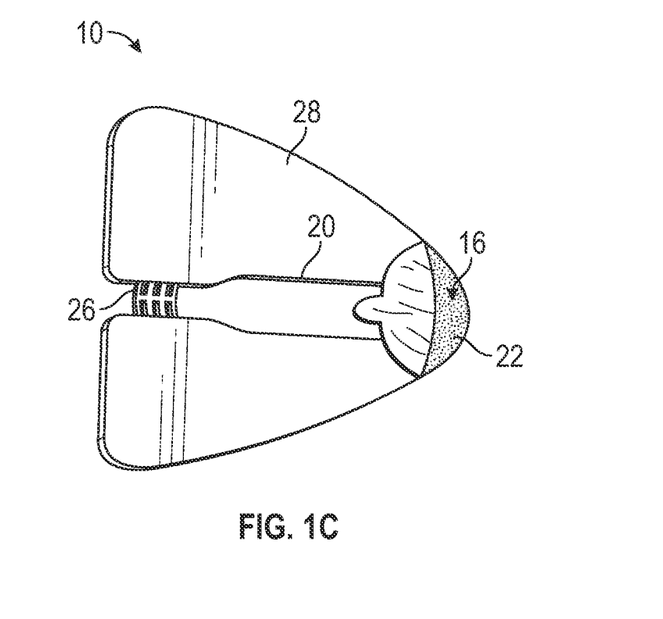
FIG. 1C is another lower perspective view of the anchor system of FIG. 1A, according to some embodiments.

Referring now to FIG. 1C, in some embodiments, the window 20 may partially enclose the insertion site, which may facilitate controlled and contained application of the skin adhesive 27 at the insertion site and allow easy attachment of the catheter 12 to the retainer 26. In some embodiments, a distal portion of the window 20 may be closed and/or a proximal portion of the window 20 may be open. In some embodiments, the window 20 may extend beneath the retainer 26. In some embodiments, an edge of the window 20 may extend to the outer edge of the anchor pad 14.

Figure 1D:
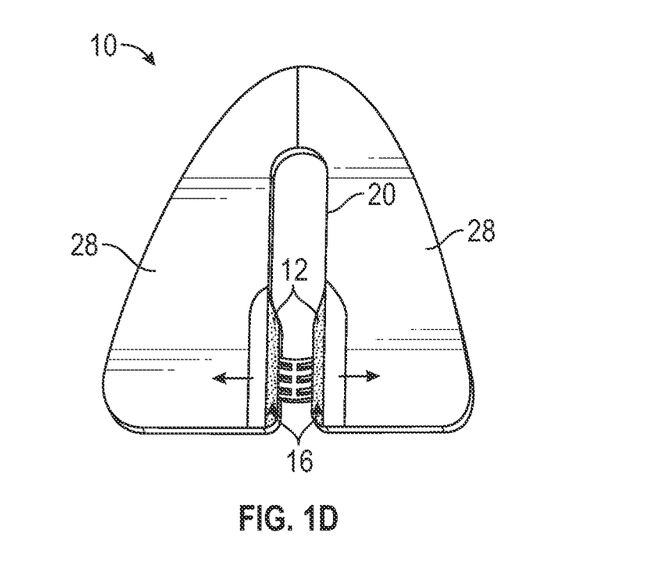
FIG. 1D is another lower perspective view of the anchor system of FIG. 1A, according to some embodiments.

Referring now to FIG. 1D, in some embodiments, the release liner may be removed by pulling or peeling the release liner 28 toward one or more sides of the anchor pad 14. The release liner 28 of FIG. 1D is divided into two pieces, according to some embodiments. In some embodiments, the release liner 28 may be divided into any number of pieces.

As discussed previously in the present disclosure, the retainer 26 may include any mechanism configured to engage and secure the catheter 12 within the retainer 26. In some embodiments, the retainer 26 may be similar to or include any suitable retainer of a StatLock® external stabilization device (Bard Medical) or another external stabilization device. FIG. 1A illustrates a peripheral IV catheter coupled to a particular retainer 26 similar to the retainer of the StatLock® IV Select Stabilization Device (Bard Medical). However, it is understood that the anchor system 10 may be utilized in connection with various types of catheters and/or retainers, a few of which are illustrated in FIGS. 2A-2E. The anchor system 10 may be utilized in connection with, for example, peripheral IV catheters, central venous catheters (CVCs), peripherally inserted central catheters (PICCs), hemodialysis catheters, arterial catheters, pediatric IV catheters, neonate IV catheters, integrated IV catheters, non-integrated IV catheters, etc.

Figure 2A:
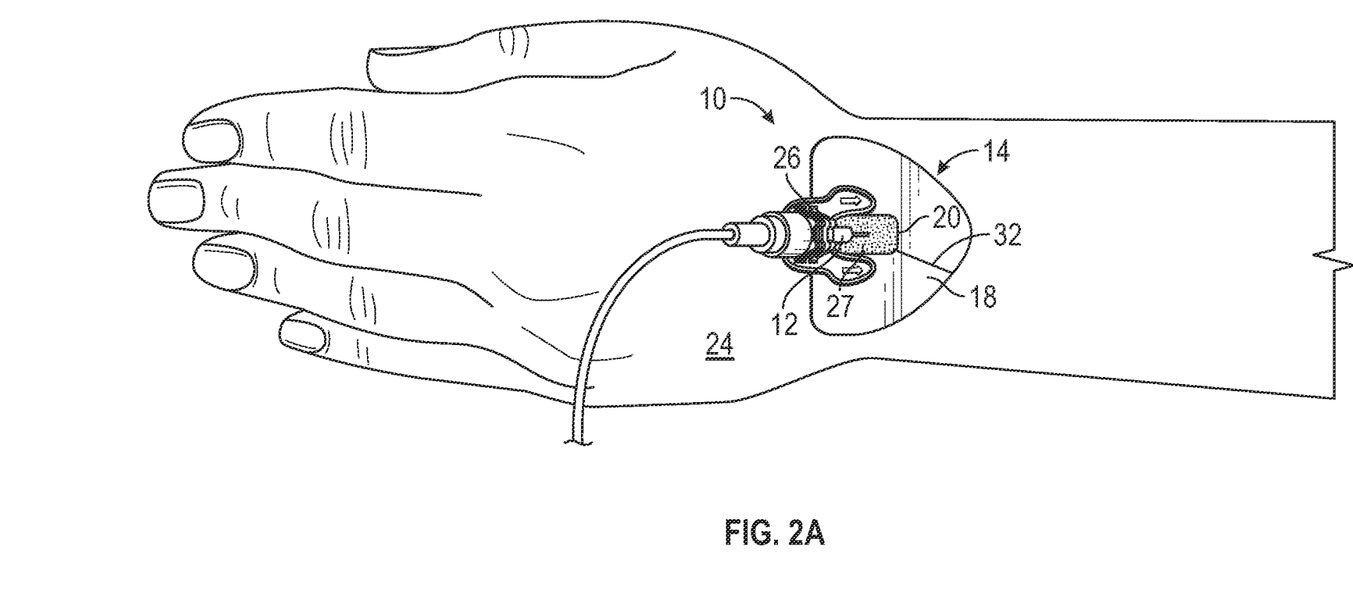
FIG. 2A is another top view of the anchor system of FIG. 1A, according to some embodiments.

FIG. 2A illustrates the anchor pad 14 coupled to a particular retainer 26 configured to secure a neonate catheter and similar to the retainer of the StatLock® IV Ultra Neonate Stabilization Device (Bard Medical), according to some embodiments.

Figure 2B:
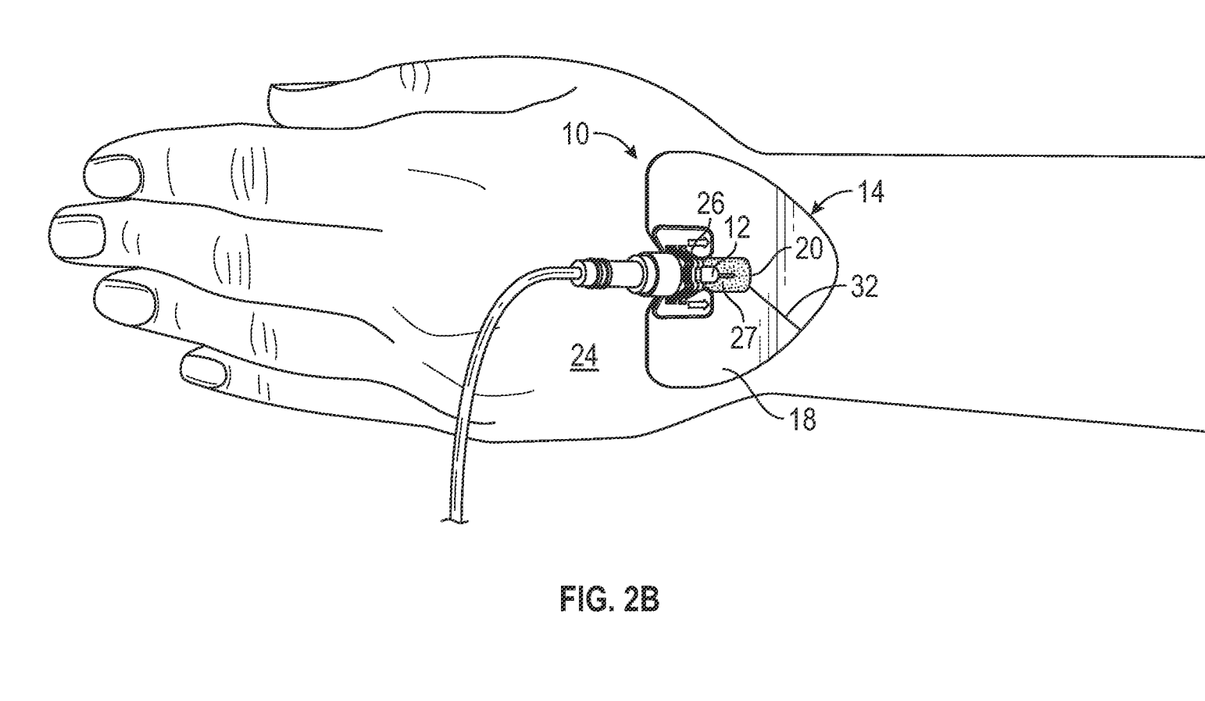
FIG. 2B is another top view of the anchor system of FIG. 1A, according to some embodiments.

FIG. 2B illustrates the anchor pad 14 coupled to a particular retainer 26 configured to secure a pediatric catheter and similar to the retainer of the StatLock® IV Ultra Pediatric Stabilization Device (Bard Medical), according to some embodiments.

Figure 2C:
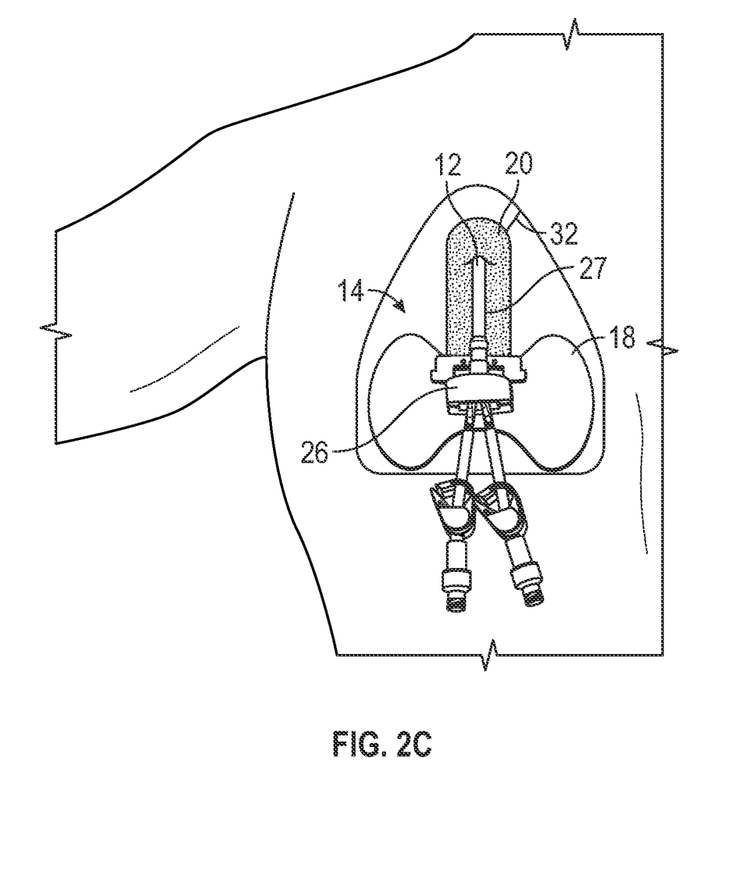
FIG. 2C is another top view of the anchor system of FIG. 1A, according to some embodiments.

FIG. 2C illustrates the anchor pad 14 coupled to a particular retainer 26 configured to secure a hemodialysis catheter and similar to the retainer of the StatLock® IV Dialysis Stabilization Device (Bard Medical), according to some embodiments.

Figure 2D:
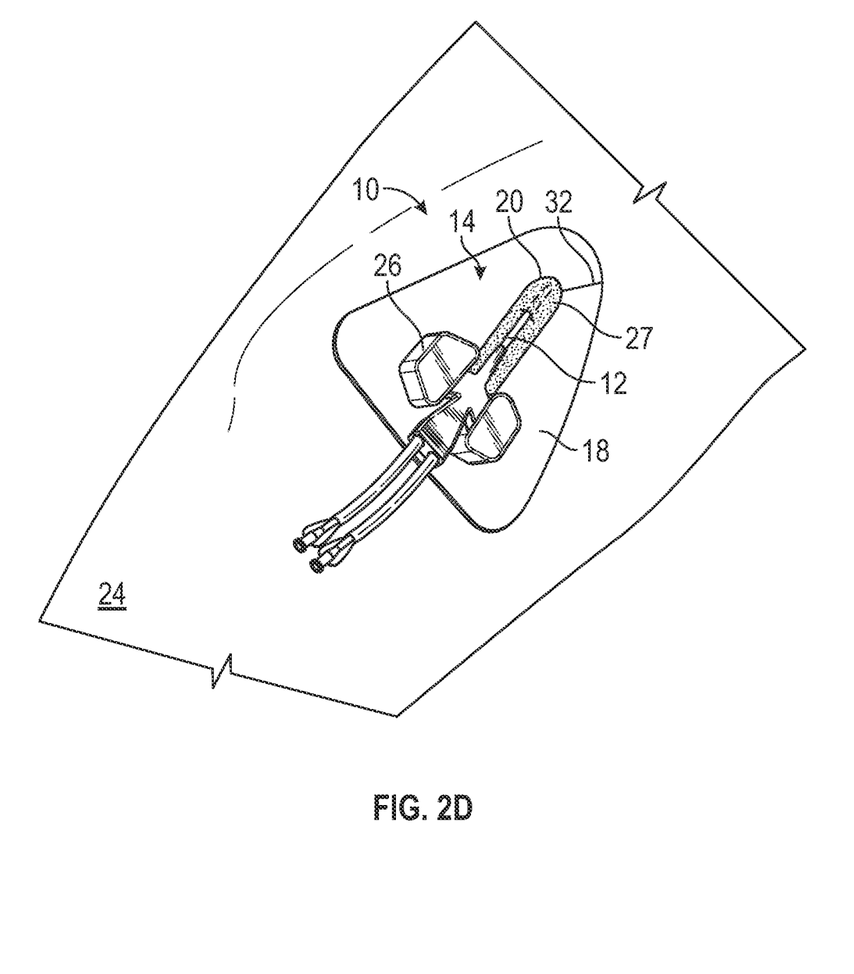
FIG. 2D is another top view of the anchor system of FIG. 1A, according to some embodiments.

FIG. 2D illustrates the anchor pad 14 coupled to a particular retainer 26 configured to secure a PICC and similar to the retainer of the StatLock® PICC Plus Stabilization Device (Bard Medical), according to some embodiments.

Figure 2E:
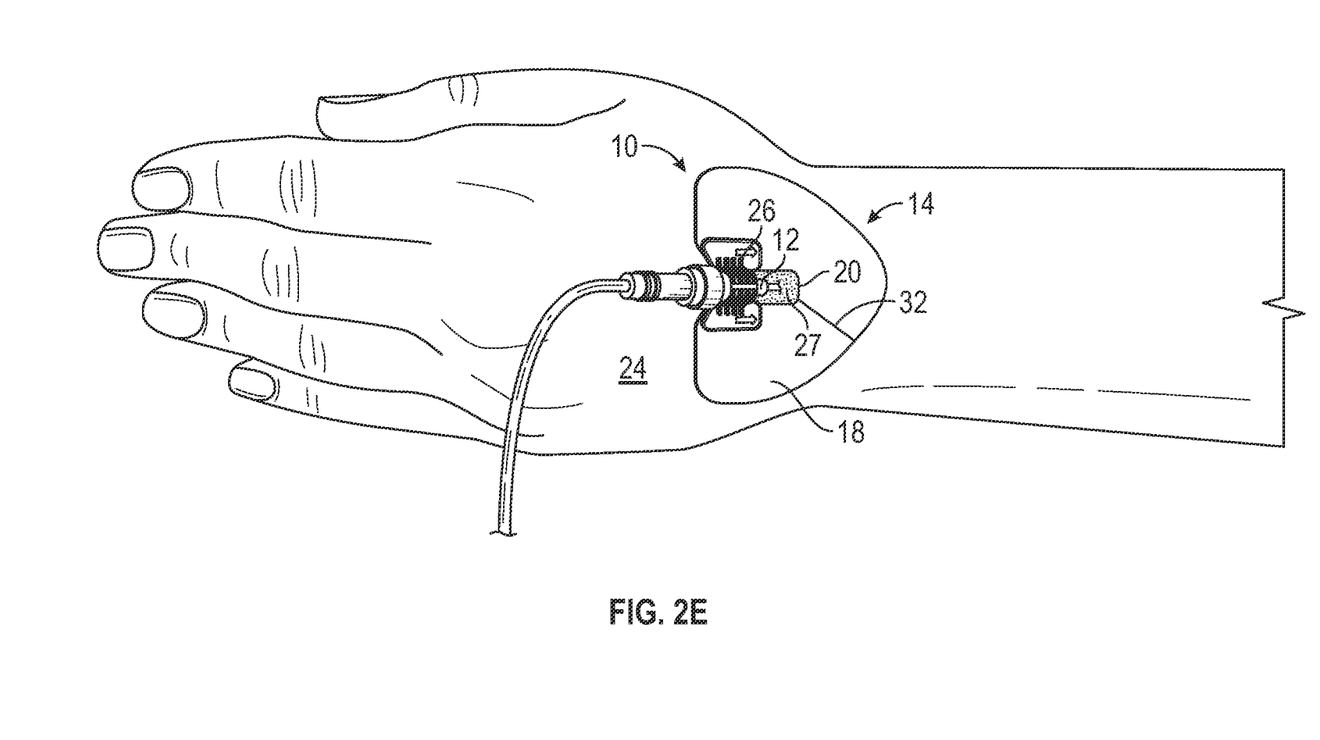
FIG. 2E is another top view of the anchor system of FIG. 1A, according to some embodiments.

FIG. 2E illustrates the anchor pad 14 coupled to a particular retainer 26 similar to the retainer of the StatLock® Arterial Select Stabilization Device (Bard Medical), according to some embodiments. In some embodiments, the window 20 illustrated in any of FIGS. 2A-2E may enclose the insertion site, as illustrated, for example, in FIG. 1B. In some embodiments, the window 20 illustrated in any of FIGS. 2A-2E may partially enclose the insertion site, as illustrated, for example, in FIG. 1C or 1D.

Figure 3A:
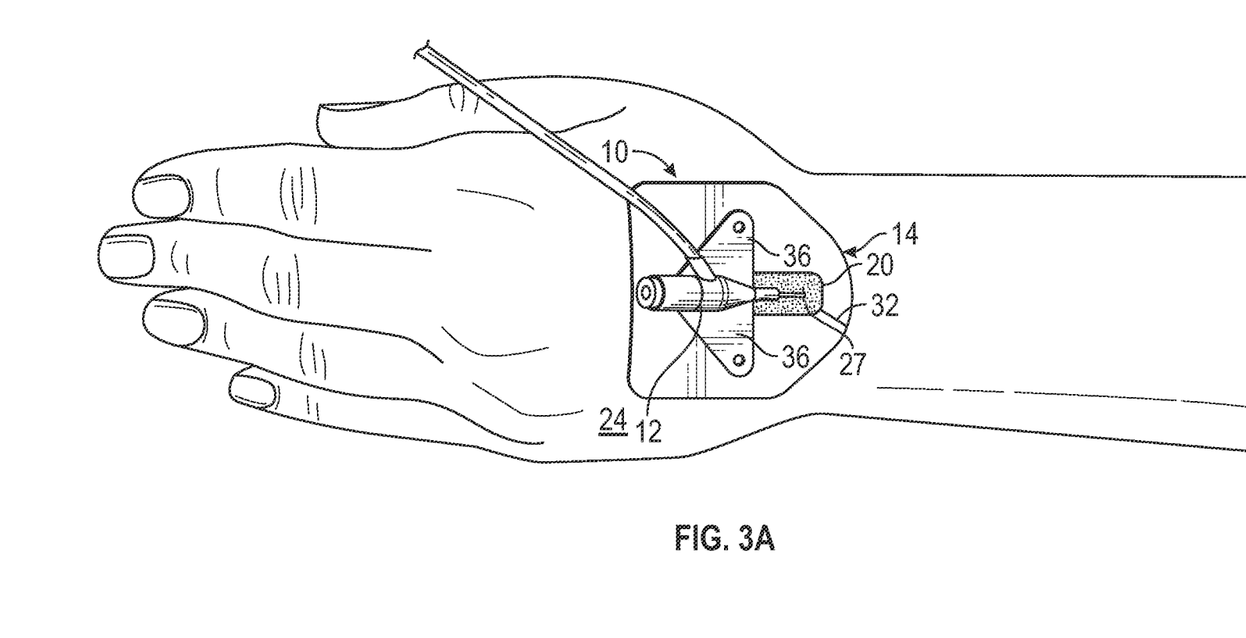
FIG. 3A is another top view of the anchor system of FIG. 1A, according to some embodiments.
Figure 3B:
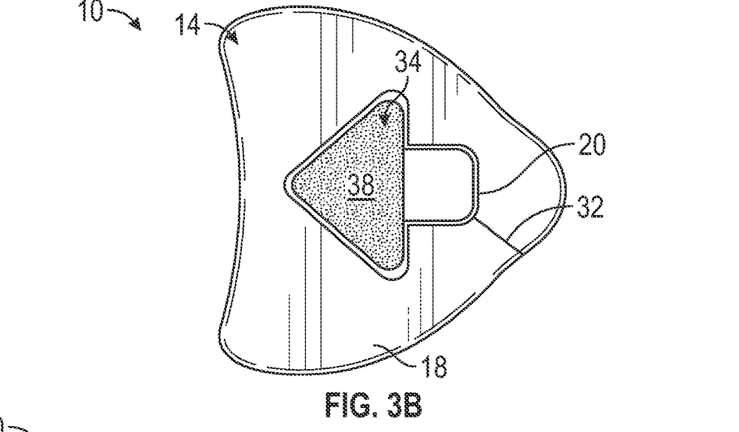
FIG. 3B is another top view of the anchor system of FIG. 1A, according to some embodiments.

Referring now to FIG. 3A-3B, in some embodiments, the anchor pad 14 of the anchor system 10 may include a recess or well 34. In these and other embodiments, including embodiments illustrated in FIGS. 2A-2E, the anchor pad may include the slit or slot 32 and/or the adhesive layer 22. In some embodiments, the well 34 may be an indentation in the anchor pad 14. In other embodiments, the well 34 may extend entirely through the pad, similar to the window 20. In some embodiments, the well 34 may have a similar shape and/or size as a portion of the catheter 12, which may include one or more stabilization platforms or wings 36. In some embodiments, the well 34 may match a foot print of the portion of the catheter 12 in shape and size.

In some embodiments, another adhesive layer 38 may be disposed within the well. For example, the adhesive layer 38 may be disposed at a bottom of the well 34. In embodiments in which the well 34 extends through the anchor pad 14, a substrate (not illustrated) may support the adhesive layer 38. In some embodiments, the portion of the catheter 12 disposed within the well 34 may be pressed into contact with the adhesive layer 38 to secure the portion of the catheter 12 to the anchor pad 14. In some embodiments, the well 34 may be proximate the window 20. In some embodiments, the well 34 may be spaced apart from the window 20.

In some embodiments, the catheter 12 may be integrated, as illustrated in FIGS. 3A-3B. For example, the catheter 12 may include the BD NEXIVA™ Closed IV Catheter (Becton, Dickinson and Company), the BD SAF-T-INTIMA™ Closed IV Catheter (Becton, Dickinson and Company), or another integrated catheter 12.

Figure 4:
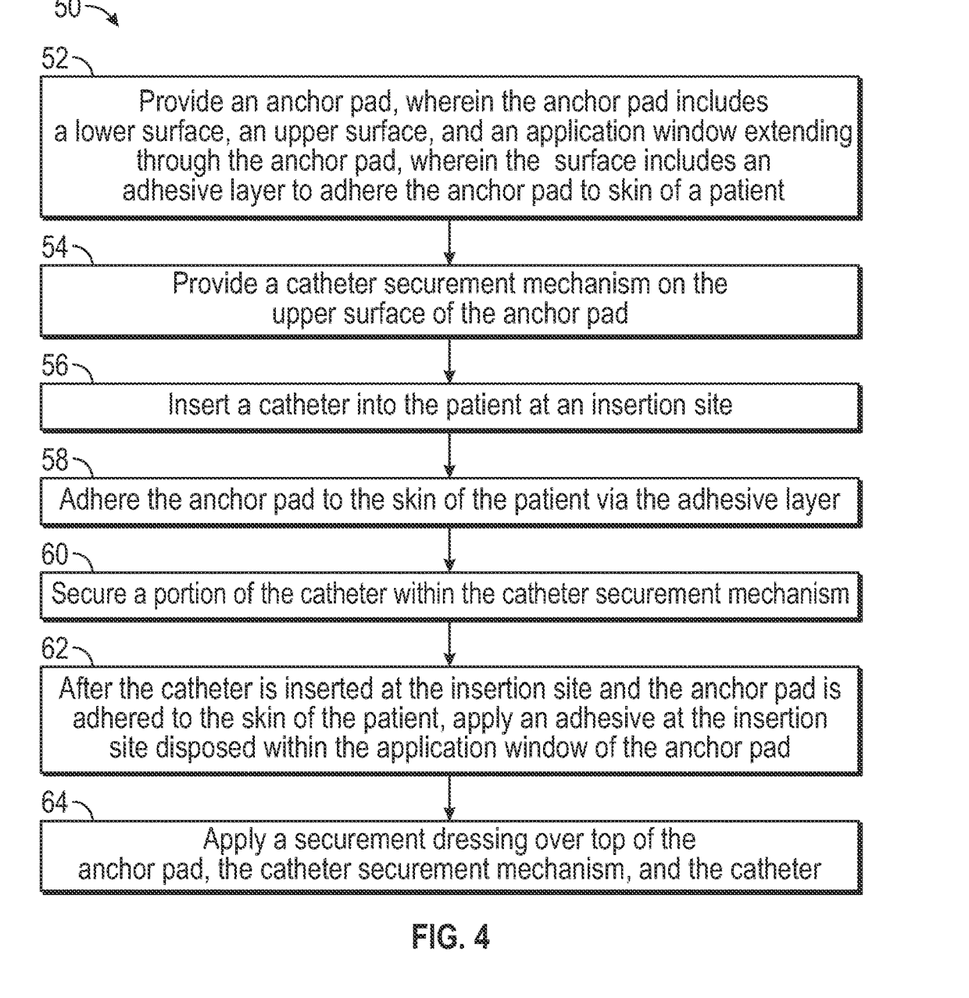
FIG. 4 is a block diagram of an example method of securing a catheter, according to some embodiments.

Referring now to FIG. 4, in some embodiments, a method 50 of securing a catheter may begin at block 52. At block 52, an anchor pad may be provided. The anchor pad may include or correspond to the anchor pad 14 discussed with respect to any of the previous FIGS. 1-3. Block 52 may be followed by block 54.

At block 54, a catheter securement mechanism may be provided. In some embodiments, the catheter securement mechanism may include a retainer and/or an adhesive well. The retainer and the adhesive well may include or correspond to the retainer 26 and the well 34, respectively, discussed with respect to any of the previous FIGS. 1-3. In some embodiments, the retainer may be coupled to the anchor pad. Block 54 may be followed by block 56.

At block 56, a catheter may be inserted into a patient at an insertion site. The catheter may include or correspond to the catheter 12 discussed with respect to any of the previous FIGS. 1-3. In some embodiments, once a distal tip of the catheter is properly placed into a blood vessel of the patient and an introducer needle is withdrawn from the blood vessel and the distal tip, the catheter may be left in place to provide intravenous access to the patient. Block 56 may be followed by block 58.

At block 58, the anchor pad may be adhered or attached to the skin of the patient via an adhesive layer disposed on a lower surface of the anchor pad. The adhesive layer may correspond to the adhesive layer 22 discussed with respect to any of the previous FIGS. 1-3. In some embodiments in which the anchor pad includes a slot, which may correspond to the slot 32 discussed with respect to FIG. 1A-1B, adhering the anchor pad to the skin of the patient via the adhesive layer may include placing an window of the anchor pad around the catheter via the slot, the catheter having been previously inserted at the insertion site. In some embodiments, adhering the anchor pad to the skin of the patient via the adhesive layer may include removing a release liner covering the adhesive layer. Block 58 may be followed by block 60.

At block 60, a portion of the catheter may be secured within the catheter securement mechanism. Block 60 may be followed by block 62.

At block 62, a skin adhesive may be applied at the insertion site and/or proximate the insertion site within the window. The skin adhesive may correspond to the skin adhesive 27 discussed with respect to any of the previous FIGS. 1-3. In some embodiments, the skin adhesive may be applied after the catheter is inserted at the insertion site and after the anchor pad is adhered to the skin of the patient. Block 62 may be followed by block 64.

At block 64, a securement dressing may be applied over top of the anchor pad, the catheter securement mechanism, and the catheter. In some embodiments, the securement dressing may include an antimicrobial agent, such as, for example, TEGADERM™ or CHLORASHIELD™.

Although illustrated as discrete blocks, various blocks may be divided into additional blocks, combined into fewer blocks, or eliminated, depending on the desired implementation. Furthermore, the order of the blocks may be changed. The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A method of securing a catheter, comprising:
inserting a catheter into a patient at an insertion site;
after inserting the catheter into the patient at the insertion site, adhering an anchor pad to skin of the patient via an adhesive layer, wherein the anchor pad comprises a lower surface, an upper surface, an opening extending through the anchor pad and enclosed within the anchor pad, and a slit extending from the opening to an outer edge of the anchor pad, wherein the lower surface comprises the adhesive layer to adhere the anchor pad to the skin of the patient, wherein the anchor pad comprises a retainer on the upper surface of the anchor pad and extending across the opening, wherein the anchor pad is adhered to the skin of the patient via the adhesive layer such that the opening is disposed over the insertion site;

securing a portion of the catheter within the retainer; and after adhering the anchor pad to the skin of the patient via the adhesive layer and after securing the portion of the catheter within the retainer, applying a liquid adhesive within the opening at the insertion site such that the liquid adhesive contacts the anchor pad and the skin of the patient within the opening.

2. The method of claim 1, further comprising curing the liquid adhesive to form a flexible or semi-rigid layer.

3. The method of claim 1, wherein adhering the anchor pad to the skin of the patient via the adhesive layer comprises removing a release liner covering the adhesive layer.

4. The method of claim 1, wherein the liquid adhesive comprises cyanoacrylate.

\* \* \* \* \*